United States Patent
Vaya et al.

(10) Patent No.: US 10,293,048 B2
(45) Date of Patent: May 21, 2019

(54) PHARMACEUTICAL COMPOSITIONS COMPRISING BORONIC ACID COMPOUNDS

(71) Applicant: DR. REDDY'S LABORATORIES LIMITED, Hyderabad (IN)

(72) Inventors: Navin Vaya, Kota (IN); Harshal Prabhakar Bhagwatwar, Hyderabad (IN); Rakeshwar Bandichhor, Chandipur (IN); Nirmal Khati, Haldwani (IN); Riyaz Ahmed Shaik, Hyderabad (IN); Rahul Bhise, Ahmednagar (IN); Yakaswamy Asalla, Warangal (IN); Rajkumar Bhimrao Shinde, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 49 days.

(21) Appl. No.: 14/382,347

(22) PCT Filed: Mar. 1, 2013

(86) PCT No.: PCT/IB2013/051644
§ 371 (c)(1),
(2) Date: Sep. 2, 2014

(87) PCT Pub. No.: WO2013/128419
PCT Pub. Date: Sep. 6, 2013

(65) Prior Publication Data
US 2015/0051172 A1 Feb. 19, 2015

(30) Foreign Application Priority Data
Mar. 2, 2012 (IN) .............................. 808/CHE/2012

(51) Int. Cl.
| | |
|---|---|
| *C07F 5/02* | (2006.01) |
| *A61K 31/69* | (2006.01) |
| *A61K 47/12* | (2006.01) |
| *A61K 47/18* | (2017.01) |
| *A61K 31/133* | (2006.01) |
| *A61K 31/194* | (2006.01) |
| *A61K 31/497* | (2006.01) |

(52) U.S. Cl.
CPC ............ *A61K 47/18* (2013.01); *A61K 31/133* (2013.01); *A61K 31/194* (2013.01); *A61K 31/497* (2013.01); *A61K 31/69* (2013.01); *A61K 47/12* (2013.01); *C07F 5/025* (2013.01)

(58) Field of Classification Search
CPC .. A61K 31/133; A61K 31/194; A61K 31/497; A61K 31/69; A61K 47/12; A61K 47/18; A61K 2300/00
See application file for complete search history.

(56) References Cited

U.S. PATENT DOCUMENTS

| | | | |
|---|---|---|---|
| 4,499,082 A | 2/1985 | Shenvi et al. | |
| 5,106,948 A | 4/1992 | Kinder et al. | |
| 5,169,841 A | 12/1992 | Kleeman et al. | |
| 5,187,157 A | 2/1993 | Kettner et al. | |
| 5,242,904 A | 9/1993 | Kettner et al. | |
| 5,250,720 A | 10/1993 | Kettner et al. | |
| 6,617,317 B1 | 9/2003 | Adams et al. | |
| 6,713,446 B2 | 3/2004 | Gupta | |
| 8,263,578 B2 | 9/2012 | Soppimath et al. | |
| 2009/0325903 A1* | 12/2009 | Elliott ..................... | C07F 5/025 514/64 |
| 2011/0178470 A1 | 7/2011 | Kocherlakota et al. | |
| 2011/0230441 A1 | 9/2011 | Soppimath et al. | |
| 2011/0275597 A1 | 11/2011 | Namdeo et al. | |
| 2012/0083457 A1 | 4/2012 | Usayapant et al. | |

FOREIGN PATENT DOCUMENTS

| | | | |
|---|---|---|---|
| CN | 102784114 A | | 11/2012 |
| EP | 2644189 A1 | | 10/2013 |
| WO | WO 2009/026427 | * | 2/2009 |
| WO | WO 2010/039762 | * | 4/2010 |

OTHER PUBLICATIONS

Bhalla (Gibaldi's Drug Delivery Systems in Pharmaceutical Care edited by Mary Lee, Archana Desai, 2007, p. 103-122).*
Bedu-Addo (Pharmaceutical Technology, Lyophilization, 2004).*
Written Opinion dated Sep. 5, 2013, for corresponding International Patent Application No. PCT/IB2013/051644.
Korcek et al., "Absolute Rate Constants for the Autoxidation of Organometallic Compounds. Part II. Benzylboranes and 1-Phenylethylboranes", J.C.S. Perkin II, 1972, pp. 242 to 248.
Snyder et al., "Aryl Boronic Acids. II. Aryl Boronic Anhydrides and their Amine Complexes", Journal of the American Chemical Society, Jul. 20, 1958, pp. 3611 to 3615, vol. 80.
Wu et al., "Degradation Pathways of a Peptide Boronic Acid Derivative, 2-Pyz-(CO)-Phe-Leu-B(OH)2", Journal of Phamaceutical Sciences, Jun. 2000, pp. 758 to 765, vol. 89-issue No. 6, Wiley-Liss, Inc. and the American Pharmaceutical Association.
International Search Report dated Sep. 5, 2013, for corresponding Patent Application No. PCT/IB2013/051644.

* cited by examiner

*Primary Examiner* — Umamaheswari Ramachandran
(74) *Attorney, Agent, or Firm* — Pergament & Cepeda LLP; Milagros A. Cepeda; Edward D. Pergament

(57) ABSTRACT

A pharmaceutical composition and preparing processes thereof. The composition comprises bortezomib or pharmaceutically acceptable salt or solvate thereof, tromethamine and an organic carboxylic acid, and the pH of the composition is from about 3.0 to 6.0.

7 Claims, 1 Drawing Sheet

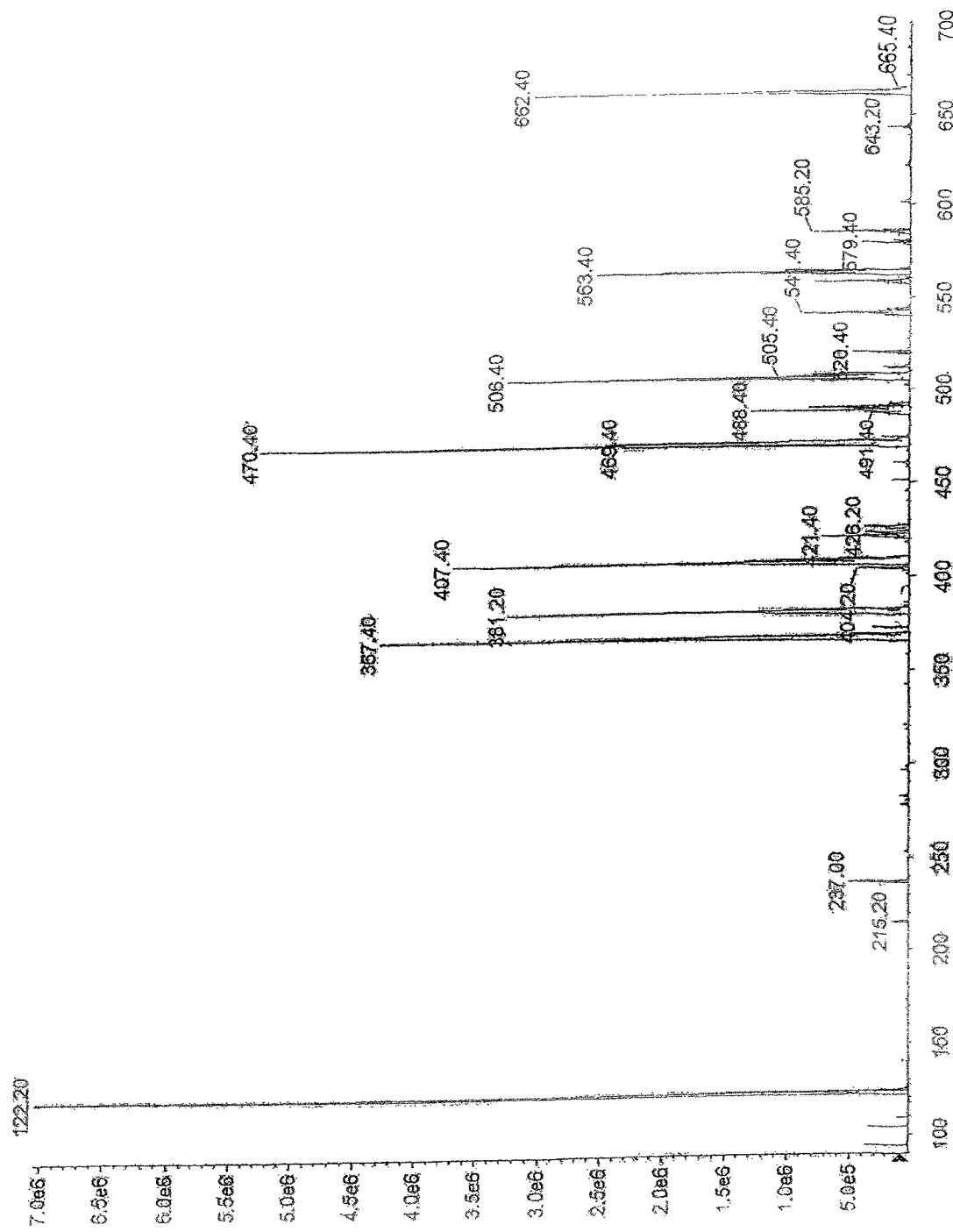

PHARMACEUTICAL COMPOSITIONS COMPRISING BORONIC ACID COMPOUNDS

This application is a National Stage Application under 35 U.S.C. § 371 of PCT International Application No. PCT/IB2013/051644 filed Mar. 1, 2013, which claims the benefit of Indian Provisional Application No. 808/CHE/2012, filed Mar. 2, 2012, all of which are hereby incorporated by reference in their entireties.

INTRODUCTION

The present invention relates to pharmaceutical compositions comprising bortezomib or pharmaceutically acceptable salt or solvate thereof, tromethamine and an organic carboxylic acid. Also included are processes for preparing such compositions and methods of using such compositions for treating various types of cancers in mammals. More specifically, the invention provides composition comprising bortezomib or pharmaceutically acceptable salt or solvate thereof, tromethamine and citric acid and its use for treating various types of cancers in mammals. The composition of the present invention is obtained by lyophilization of a mixture comprising N-(2-pyrazine) carbonyl-L-phenylalanine-L-leucine boronic acid (i.e. Bortezomib) or pharmaceutically acceptable salt or solvate thereof, tromethamine and an organic carboxylic acid.

A boronic acid is an alkyl or aryl substituted boric acid containing a carbon-to-boron chemical bond belonging to the larger class of organo-boranes. Boronic acids act as Lewis acids. They have the unique feature of being capable of forming reversible covalent complexes with sugars, amino acids, hydroxamic acids, etc. (molecules with vicinal, (1,2-) or occasionally (1,3-) substituted Lewis base donors (alcohol, amine, carboxylate)). Though the $pK_a$ of a boronic acid is about 9, they form tetrahedral boronate complexes with $pK_a$ about 7 upon complexion in aqueous solutions.

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993), U.S. Pat. No. 5,242,904 (1993) and U.S. Pat. No. 5,250,720 (1993) describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain tripeptide boronic acid compounds inhibit the growth of cancer cells.

Unfortunately, alkylboronic acids are relatively difficult to obtain in analytically pure form. The reference H. R. Snyder et al., "Aryl Boronic Acids. II. Aryl Boronic Anhydrides and their Amine Complexes," *Journal of the American Chemical Society*, Vol. 80, 3611-3615 (1958), teaches that alkylboronic acid compounds readily form boroxines (anhydrides) under dehydrating conditions. Also, alkylboronic acids and their boroxines are often air-sensitive. The reference S. Korcek et al., "Absolute Rate Constants for the Autoxidation of Organometallic Compounds. Part II. Benzylboranes and 1-Phenylethylboranes," *Journal of the Chemical Society, Perkin Transactions* 2, pp. 242-248 (1972), provides that butylboronic acid is readily oxidized by air to generate 1-butanol and boric acid. These difficulties limit the shelf life and the pharmaceutical utility of boronic acid compounds.

The chemical name for bortezomib, the monomeric boronic acid, is [(1R)-3-methyl-1-[[(2S)-1-oxo-3-phenyl-2-[(pyrazinylcarbonyl)amino]propyl]amino]butyl]boronic acid. The solubility of bortezomib, as the monomeric boronic acid, in water is 3.3 to 3.8 mg/mL over a pH range of 2 to 6.5. Bortezomib has the chemical structure below.

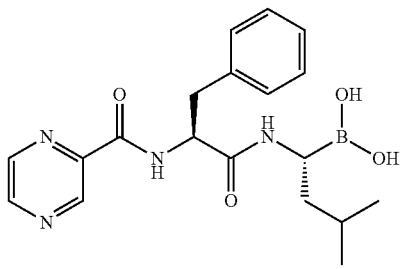 [SMILES: CC(C)C[C@H](NC(=O)[C@H](Cc1ccccc1)NC(=O)c1cnccn1)B(O)O]

Bortezomib is a reversible inhibitor of the chymotrypsin-like activity of the 26S proteasome in mammalian cells. The 26S proteasome is a large protein complex that degrades ubiquitinated proteins. The ubiquitin-proteasome pathway plays an essential role in maintaining homeostasis within cells by regulating the intracellular concentration of specific proteins. Inhibition of the 26S proteasome prevents this targeted proteolysis, which can affect multiple signaling cascades within the cell. This disruption of normal homeostatic mechanisms can lead to cell death.

Bortezomib is a modified di-peptidyl boronic acid. It is the first therapeutic proteasome inhibitor to be tested in humans. The product is provided commercially as a mannitol boronic ester, which in reconstituted form consists of the mannitol ester in equilibrium with its hydrolysis product, the monomeric boronic acid. The drug substance exists in its cyclic anhydride form as a trimeric boroxine in solid state.

Commercially, bortezomib is sold as mannitol ester under the brand name VELCADE® which is supplied as a sterile lyophilized powder for intravenous infusion and available in single-dose vials. As per the label of VELCADE approved by FDA, each single dose vial contains 3.5 mg of bortezomib as a sterile lyophilized powder. The inactive ingredient is 35 mg mannitol USP per vial. VELCADE® when reconstituted forms a solution consisting of the mannitol ester in equilibrium with bortezomib. Velcade® is reconstituted with 0.9% sodium chloride to a final concentration of 1 mg/ml of bortezomib. The prescribing information (Physician Desk Reference, published by Thomson Healthcare, 62 edition, 2008, pp. 2151-2157) provides that the reconstituted product should be clear and colorless and should be visually inspected for particulate matter and discoloration and only clear solution which is not discolored should be used within eight hours after preparation. This guidance is in view of the extreme precautions required in administering drugs directly into the intravenous system. Formation of particles is undesirable and preparations should meet high purity requirements.

U.S. Pat. No. 6,713,446 describe pharmaceutical compositions of boronic acid compounds prepared by lyophilizing an aqueous mixture comprising a boronic acid compound and a sugar such as mannitol that readily releases the boronic acid compound upon dissolution in aqueous media.

U.S. Pat. No. 6,617,317 discloses a method for reducing the rate of degradation of proteins in an animal comprising contacting cells of the animal with certain boronic ester and acid compounds. Also disclosed are novel boronic ester and acid compounds, their synthesis and uses.

PCT Publication No WO2010/089768 discloses pharmaceutical composition comprising bortezomib and tromethamine in lyophilized form which is stable at room temperature and upon reconstitution forms aqueous solutions that are stable for at least 12 hours. According to the application, it is critical that the pH of the solution containing bortezomib and tromethamine to be subjected to lyophilisation for the preparation of composition should be adjusted in the range of 7.6 to 8.4. It was found that when the pH was adjusted beyond this specified range, particles were formed in the reconstituted solution indicating precipitation of bortezomib and/or the time taken for preparation of reconstituted solution from the lyophilized cake was more than desired.

Sara Wu et al J. Pharm Sci 89 (6), 2000; pp. 758-765 has reported the effect of ascorbic acid and EDTA on the bortezomib stability. The authors have determined the effects of ascorbic acid on the stability of 2-Pyz-(CO)-Phe-Leu-B(OH)2, for which the compound (1.3 mM) was dissolved in a mixed solvent of 2% Ethyl-alcohol and 98% normal saline (pH 2.8, adjusted with hydrochloric acid) with and without 5.7 mM ascorbic acid. The solutions were sealed in ampules and incubated at 25° C. The samples were analyzed after 5 and 14 days, respectively. Under acidic and basic conditions, it was observed that impurity D-an oxidative impurity was a major degradant. After storage for 14 days, the sample containing 0.1% of ascorbic acid experienced 21.8% degradation, whereas the sample containing no ascorbic acid showed only 5.9% degradation. The results suggested that ascorbic acid actually accelerated the degradation of 2-Pyz-(CO)-Phe-Leu-B (OH) 2.

There remains a need of composition comprising bortezomib or pharmaceutically acceptable salt or solvate thereof with properties which improve its utility as a pharmaceutical agent. Ideally, such composition would be conveniently prepared, would exhibit enhanced stability and longer shelf life and would readily liberate the bioactive boronic acid compound when administered to a subject in need of boronic acid therapy. Surprisingly, inventors of the present application have developed compositions comprising bortezomib or pharmaceutically acceptable salt or solvate thereof, tromethamine and an organic carboxylic acid with improved properties. The compositions of the present invention are obtained by lyophilization of a mixture comprising bortezomib or pharmaceutically acceptable salt or solvate thereof, tromethamine and an organic carboxylic acid. Preferably, the composition comprises bortezomib, tromethamine and citric acid. The compositions of the present invention remains stable during the product shelf life, does not pose solubility problems upon reconstitution and the reconstituted solutions have improved stability.

SUMMARY

The present invention relates to pharmaceutical compositions comprising bortezomib or pharmaceutically acceptable salt or solvate thereof, tromethamine and an organic carboxylic acid.

Preferably, the composition of the present invention comprises bortezomib, tromethamine and citric acid.

Also included are processes for preparing such compositions and methods of using such compositions for treating various types of cancers in mammals.

An aspect of the present invention provides a method of producing a pharmaceutical composition comprising bortezomib or pharmaceutically acceptable salt or solvate thereof, tromethamine and an organic carboxylic acid by lyophilization of a mixture comprising bortezomib or pharmaceutically acceptable salt or solvate thereof, tromethamine and an organic carboxylic acid. The solutions made by dissolving such compositions in a suitable solvent, preferably water, form another aspect of the invention. The pH of the reconstituted solution is from about 3.0 to 6.0. Preferably, the pH is from about 3.5 to 5.5. More preferably the pH is from about 4.0 to 4.5.

Another aspect of the present invention provides a pharmaceutical composition obtained by lyophilization of bortezomib or pharmaceutically acceptable salt or solvate thereof, tromethamine and an organic carboxylic acid, wherein the total impurities in the pharmaceutical composition are less than 3% over a period of 3 months at 40° C./75% RH.

The present invention further relates to the compound of formula (I).

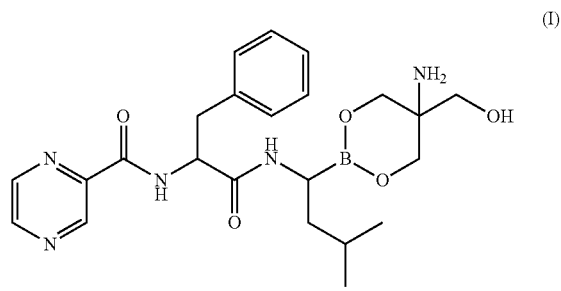 [SMILES: CC(C)CC(NC(=O)C(Cc1ccccc1)NC(=O)c1cnccn1)B1OCC(N)(CO)CO1]

Compound (I) is tromethamine ester of bortezomib and is formed by lyophilization of a mixture comprising bortezomib or pharmaceutically acceptable salt or solvate thereof, tromethamine an organic carboxylic acid according to the process of the present invention.

The present invention also relates to compound of formula (II), the esters of bortezomib with organic carboxylic acids.

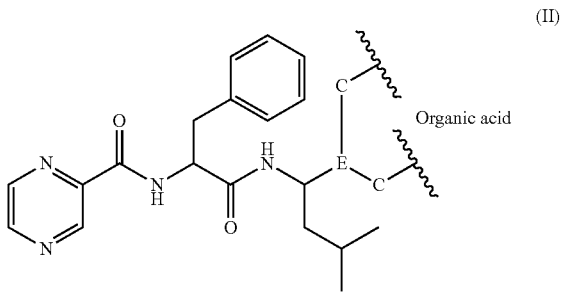

Preferably, the compound of formula (II) is the compound of formula (IIa) of the following structure.

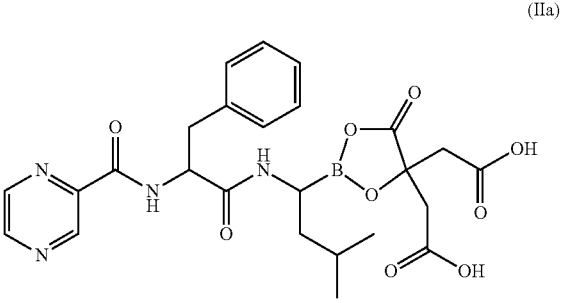 [SMILES: CC(C)CC(NC(=O)C(Cc1ccccc1)NC(=O)c1cnccn1)B1OC(=O)C(CC(=O)O)(CC(=O)O)O1]

The compound of formula (II) is formed by lyophilization of a mixture comprising bortezomib or pharmaceutically acceptable salt or solvate thereof, tromethamine and an organic carboxylic acid according to the process of the present invention. The compound of formula (IIa) is formed by lyophilization of a mixture comprising bortezomib or pharmaceutically acceptable salt or solvate thereof, tromethamine and citric acid.

Another aspect of the present invention provides a composition, which further comprises compound of formula (I) and compound of formula (II) in addition to bortezomib or pharmaceutically acceptable salt or solvate thereof, tromethamine and an organic carboxylic acid. Preferably, the composition comprises bortezomib, tromethamine, citric acid, compound of formula (I) and compound of formula (IIa).

Another aspect of the present invention provides a method of preparation of a composition comprising bortezomib or pharmaceutically acceptable salt or solvate thereof, tromethamine and an organic carboxylic acid comprising lyophilization of a mixture comprising bortezomib or pharmaceutically acceptable salt or solvate thereof, tromethamine and an organic carboxylic acid.

The method comprising:
(a) Preparation of mixture/s comprising tromethamine and/or an organic carboxylic acid and suitable solvent
(b) Preparation of mixture comprising bortezomib or pharmaceutically acceptable salt or solvate thereof and suitable solvent
(c) Mixing the products of steps (a) & (b), and
(d) Lyophilizing the product of step c.

Preferably, the composition comprises bortezomib or pharmaceutically acceptable salt or solvate thereof, tromethamine, citric acid, compound of formula (I) and compound of formula (II). More preferably, the composition comprises bortezomib, tromethamine, citric acid, compound of formula (I) and formula (IIa).

Another aspect of the present invention provides a composition comprising bortezomib or pharmaceutically acceptable salt or solvate thereof, compound of formula (I) and compound of formula (II). More preferably, the composition comprises bortezomib, compound of formula (I) and formula (IIa).

BRIEF DESCRIPTION OF THE DRAWING

FIG. 1 is a Mass spectra obtained for composition as per the Example: 1

DETAILED DESCRIPTION

The present invention relates to pharmaceutical compositions comprising bortezomib or pharmaceutically acceptable salt or solvate thereof, tromethamine and an organic carboxylic acid. Preferably, the organic carboxylic acid is citric acid.

Also included are processes for preparing such compositions and methods of using such compositions for treating various types of cancers in mammals.

The compositions of the present invention comprise bortezomib or pharmaceutically acceptable salt or solvate thereof, tromethamine and an organic carboxylic acid. Preferably, the composition of the present invention comprises bortezomib or pharmaceutically acceptable salt or solvate thereof, tromethamine and citric acid. More preferably, the composition of the present invention comprises bortezomib, tromethamine and citric acid.

The compositions of the present invention are prepared by a method comprising of the following steps:
(a) Preparation of mixture/s comprising tromethamine and/or an organic carboxylic acid and suitable solvent
(b) Preparation of mixture comprising bortezomib or pharmaceutically acceptable salt or solvate thereof and suitable solvent
(c) Mixing the products of steps (a) & (b), and
(d) Lyophilizing the product of step c.

Step (a): Preparation of Mixture/s Comprising Tromethamine and/or an Organic Carboxylic Acid and Suitable Solvent The first step, preferably, in the process of the present invention is preparation of mixture/s comprising tromethamine and/or citric acid and suitable solvent. Tromethamine and citric acid can be present in a single mixture with a suitable solvent or they can be present in different mixtures with same or different suitable solvents. The mixture/s can be prepared by addition of tromethamine and/or organic carboxylic acid, either separately or together in a suitable solvent. The addition is preferably done at ambient temperature. The order of addition of tromethamine and organic carboxylic acid is immaterial for the purpose of the preparation of the mixture, if such mixture is intended to comprise both tromethamine and citric acid. If mixtures of tromethamine and organic carboxylic acid with suitable solvents are prepared in two different containers separately, they are mixed after they are prepared. Addition of independent mixtures of tromethamine and organic carboxylic acid with suitable solvents separately to the mixture of bortezomib with suitable solvent of step (b) is contemplated as part of the process of the present invention. The volume of the suitable solvent to be used for this purpose can be determined by persons of ordinary skilled in the art. The mixture may be heterogeneous or homogeneous. Preferably, the volume of the solvent should be such that it forms a clear solution. If the mixture is a heterogeneous solution, such heterogeneous solution may become clear upon mixing with the mixture obtained in step b).

Step (b): Preparation of Mixture Comprising Bortezomib or Pharmaceutically Acceptable Salt or Solvate Thereof and Suitable Solvent The next step, preferably, in the process of the present invention is preparation of mixture comprising bortezomib or pharmaceutically acceptable salt or solvate thereof and suitable solvent. It is done by mixing bortezomib or pharmaceutically acceptable salt or solvate thereof with a suitable solvent. The mixing is preferably done at ambient temperature. It is possible that such mixing process may yield a heterogeneous solution, which upon mixing with the solution of step a) may lead to the formation of a clear solution. The volume of the suitable solvent to be used for this purpose can be determined by persons of ordinary skilled in the art. Preferably, the volume of the solvent should be such that it forms a clear solution.

The steps (a) and (b) of the process of the present invention may be done either sequentially or simultaneously.

(c) Mixing the Product's of Step (a) & (b)

Mixing of mixtures of steps a) and b) is preferably done at ambient temperature. Generally, this mixing leads to the formation of a clear solution. If the mixing of mixtures of steps a) and b) leads to the formation of heterogeneous solution, preferably, further amount of suitable solvent is added to get the clear solution before subjecting the mixture to lyophilization.

Preferably, the ratio of bortezomib:tromethamine:organic carboxylic acid to be used in the process of the present invention may vary from 1:1-15:1-11 molar equivalents. More preferably the ratio of bortezomib:tromethamine:organic carboxylic acid is 1:4-10:4-8 molar equivalents. Most preferably the ratio of bortezomib:tromethamine:organic carboxylic acid is 1:7-8:5-6 moles.

The term 'organic carboxylic acid' refers to the pharmaceutically acceptable organic acids containing —COOH groups. Examples of organic carboxylic acids include citric acid, succinic acid, lactic acid, tartaric acid, fumaric acid, maleic acid and malic acid. Mixtures of acids can also be used for the process of the present invention. The preferred organic carboxylic acid is citric acid.

The term suitable solvent refers to any organic solvent or water or mixtures thereof. The term "organic solvent" refers to any organic solvent that can be evaporated under lyophilization conditions. Examples of organic solvents include alcohols (primary, secondary or tertiary such as ethanol, Iso propyl alcohol, tertiary butyl alcohol), esters such as methyl acetate, ethyl acetate, nitriles such as acetonitrile, halocarbons such as dichloromethane, carbon tetrachloride, ketones such as acetone, methyl ethyl ketone, methyl isobutyl ketone, hydrocarbons such as cyclohexane, and other polar solvents such as dimethylsulfoxide, dimethylsulfone, acetic acid, etc., Mixtures of organic solvents, either alone or in combination with water, may be used for lyophilization. Organic solvents may act as co-solvent when used in combination with water. Water alone may also be used for lyophilization. Preferred solvents are mixture of water with one or more organic solvents. More preferred are mixtures of water with alcohol, acetone or acetonitrile. Most preferred solvent is mixture of water and acetonitrile.

Optionally, before subjecting the mixture of step c) to lyophilization, one or more pharmaceutically acceptable excipients such as preservatives such as benzalkonium chloride and methyl paraben, anti-oxidants such as EDTA or Butyl hydroxy toluene, isotonicity agents such as sodium chloride or dextrose etc may be added to the mixture. Optionally, other pharmaceutical excipients such as diluents, fillers, stabilizers may also be added to the mixture.

The pH of the mixture from step c) preferably is from about 3.0 to 6.0. More preferably, the pH is from about 3.5 to 5.5. Most preferably, the pH is from about 4.0 to 4.5.

(d) Lyophilizing the Product of Step c)

Lyophilization or freeze drying is defined as a process in which solvent is removed from a mixture after it is frozen and placed under vacuum allowing the frozen solvent to change directly from solid to vapor phase without passing through a liquid phase. The process consists of three separate, unique, and interdependent processes; freezing, primary drying (sublimation), and secondary drying (desorption). In this process, the moisture content of the product is reduced to such a low level that it does not support biological growth or chemical reactions.

Lyophilization or freeze drying process generally involves removal of the solvent system from the solution under vacuum leaving a highly porous material. This increase in porosity results in higher dissolution rate leading to improved solubility of the drug. Lyophilization of drugs with suitable excipients also results in a high degree of interaction between the two which can further improve the solubility of poorly soluble drugs. For lyophilized product, reconstitution time and reconstituted solution clarity are good indicators of improved nature of the product.

Lyophilization involves two steps namely, thermal treatment step wherein no vacuum is applied and the actual primary drying step wherein vacuum is applied. The solution to be subjected to lyophilization is filled into vials with specialized stoppers. The vials filled with the solution to be dried are placed in the lyophilizer. In the thermal treatment step, temperature of shelf of lyophilizer where the vials of solution filled is stored is gradually reduced to −40° C. Then the frozen solution is subjected to drying step. For example, in this instance, the temperature is set from −40° C. to −15° C. for the time cycle of about 5 to 6 hours at a vacuum of about 100 to 200 mTorr. At this time and temperature, the frozen solvent is dried. Then the temperature of the material is raised to +10° C. to about +25° C. at a vacuum of about 50 mTorr in which the residual solvent, if any, is removed. The lyophilized composition or commonly referred to as lyophilized cake generally will be in the form of a free flowing powder.

Single lyophilization cycle generally yields satisfactory results in the process of the present invention. However, one skilled in the art would appreciate that certain condition of first lyophilization may warrant second lyophilization to obtain the desired results.

It is preferred that the pharmaceutical composition of the present invention is sterilized. Preferably, it is done by subjecting the solution from step c) to micron-sterile filtration, before the step of lyophilization.

A suitable means for sealing the vial can include, for example, a stopper, a cap, a lid, a closure, a covering which fluidly seals the vial, or the like. The means for sealing the vial are not limited to separate closures or closure devices. The means for aseptically sealing the vial includes a stopper such as, for example, a stopper that is configured to fluidly seal the opening. Suitable stoppers include conventional medical grade stoppers which do not degrade or release significant amounts of impurities upon exposure to the reconstituted aqueous bortezomib solution. Preferably, the stopper is constructed of an elastomer, which is more preferably an elastomer that is pierceable by a hypodermic needle or a blunt cannula. Exemplary stoppers include 6720 GC gray rubber stoppers from American Stelmi Corporation, 4432/50 gray rubber stoppers from West Company, and the like.

Optionally, an outer seal is provided which covers and entirely surrounds the stopper. The outer seal can be constructed of any suitable material. When an outer seal is used, it is preferably fitted with a lid that can be easily manually removed to provide access to the stopper. Suitable outer seals can include, for example, flip-off aluminum/polypropylene seals (lacquered or non-lacquered aluminum), such as are marketed by The West Company, Inc., and other manufacturers. Such seals include an outer rim made of a suitable material, such as aluminum, that entirely surrounds the lateral edge of the stopper and further include a lid (typically polypropylene or other suitable material) that entirely covers the upper surface of the stopper. The polypropylene lid can be "flipped" off, e.g., by exerting upward pressure with a finger or thumb, to provide access to the stopper, so that it can be punctured with a hypodermic needle to deliver an aqueous vehicle for constitution. Optionally, the seal can be removed in its entirety to allow the powder to be poured from the vial.

The compositions of the present invention may optionally comprise compound of formula (I) and compound of formula (II), in addition to bortezomib or pharmaceutically acceptable salt thereof, tromethamine and an organic carboxylic acid. Preferably, the composition of the present invention comprise bortezomib, tromethamine, citric acid, compound of formula (I) and compound of formula (II). Most preferably, the composition of the present invention comprise bortezomib, tromethamine, citric acid, compound of formula (I) and compound of formula (IIa). The composition is prepared by lyophilization of bortezomib or pharmaceutically acceptable salt or solvate thereof, tromethamine and an organic carboxylic acid. More preferably, the composition is prepared by lyophilization of bortezomib or pharmaceutically acceptable salt or solvate thereof, tromethamine and citric acid.

The present invention further relates to the following compounds (I) and (II).

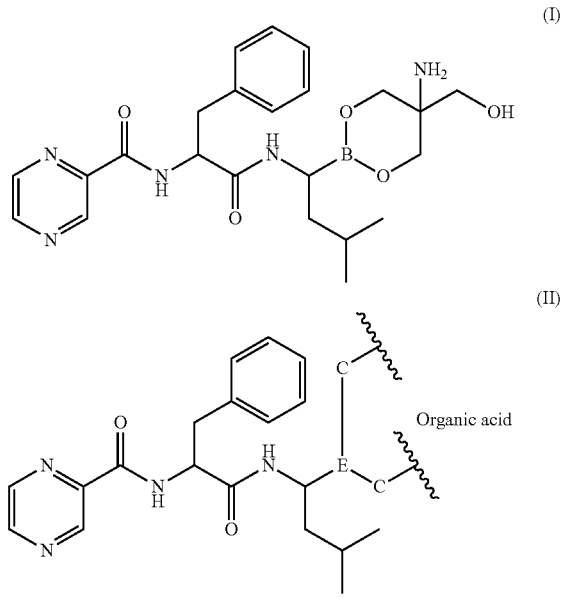

Preferably, the compound of formula (II) is the compound of formula (IIa) of the following structure.

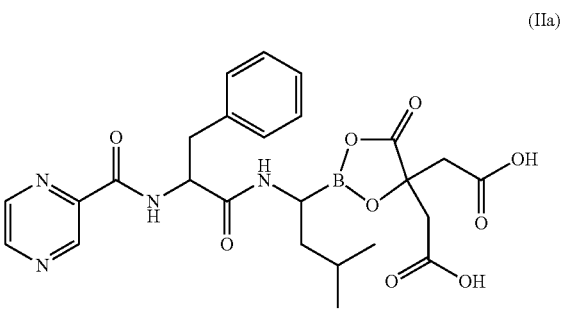 [SMILES: CC(C)CC(NC(=O)C(Cc1ccccc1)NC(=O)c1cnccn1)B1OC(=O)C(CC(=O)O)(CC(=O)O)O1]

Compound (I) is tromethamine ester of bortezomib, compound (II) is the organic carboxylic acid ester of bortezomib and compound (IIa) is the citric acid ester of bortezomib.

Compound (I) is formed by lyophilization of a mixture comprising bortezomib or pharmaceutically acceptable salt or solvate thereof, tromethamine and an organic carboxylic acid according to the process of the present invention. Preferably, the organic carboxylic acid is citric acid.

Compound (II) is also formed by lyophilization of a mixture comprising bortezomib or pharmaceutically acceptable salt or solvate thereof, tromethamine and an organic carboxylic acid according to the process of the present invention. Compound (IIa) is formed by lyophilization of a mixture comprising bortezomib or pharmaceutically acceptable salt or solvate thereof, tromethamine and citric acid according to the process of the present invention.

Another aspect of the present invention provides a composition comprising bortezomib or pharmaceutically acceptable salt or solvate thereof, compound of formula (I) and compound of formula (II). More preferably, the composition comprises bortezomib, compound of formula (I) and compound of formula (IIa).

The lyophilized compositions of the present invention are stable with better reconstitution time and the reconstituted solution has advantageous impurity profile upon storage.

The compositions of the present invention have sufficient stability to have utility as a pharmaceutical agent. Preferably, the formulation has sufficient stability to allow its storage at a convenient temperature, preferably between 0° C. and 40° C., for a reasonable period of time. Preferably, the total impurities in the pharmaceutical composition are less than 3% over a period of 3 months at 40° C./75% RH. Further, the pharmaceutical composition of the present invention when in the form of a lyophilized cake or powder that is the composition is not reconstituted remains unaltered in terms of physical and chemical parameters for a prolonged period of time when packed in container, for instance when stored at 25° C./60% RH and 40° C./75% RH.

The lyophilized product is generally reconstituted with 1.4 ml/3.5 ml of 0.9% sodium chloride solution for sub cutaneous/intravenous route of administration respectively; which is immediately dispersed into the reconstitution solvent. The lyophilized preparations of the present invention are readily reconstituted in about 120 seconds or less to form clear, near-colorless to colorless solutions that are free of discoloration (i.e., are colorless or near colorless) and/or particulate matter, suitable for injection into humans. Preferably, the time taken for reconstitution is about 90 seconds or less. More preferably, the time taken for reconstitution is about 60 seconds or less. Most preferably, the time taken for reconstitution is about 30 seconds or less.

The pharmaceutical composition of the present invention when reconstituted with a suitable reconstitution medium such as water for injection, the reconstituted solution remains clear with no signs of precipitation or appearance of particles on storage at room temperature for at least 12 hours, preferably 24 hours.

The formulations of the present invention are particularly suited for use in parenteral administration. Injectable formulations may take any route including intramuscular, intraperitoneal, intravenous or subcutaneous administration. Preferred are subcutaneous or intravenous route of administration for the composition of the present invention.

Injectable formulations are typically formulated as aqueous solutions in which water is the primary excipient. The compositions of the present invention can be reconstituted with water for injection. Water for injection may further contain a solute such as dextrose or sodium chloride for the purpose of reconstitution. Illustratively, 0.9% sodium chloride injection USP, bacteriostatic 0.9% sodium chloride injection USP, 5% dextrose injection USP, and 5% dextrose and 0.45% sodium chloride injection USP are suitable.

The following examples further describe certain specific aspects and embodiments of the invention and demonstrate the practice and advantages thereof. It is to be understood that the examples are given by way of illustration only and are not intended to limit the scope of the invention in any manner.

EXAMPLES

Example 1

| Drug/Excipient | Formulation F1<br>Quantity (mg) per vial |
|---|---|
| Bortezomib | 3.5 mg |
| TRIS | 8.4 mg |
| Citric Acid | 10.0 mg |
| Acetonitrile* | 2 mL. |
| Water for injection* | 2 mL. |
| pH on reconstitution | 3.5-6.0 |

*Water for Injection and Acetonitrile does not remain in the final formulation as it is removed during Lyophilization
Primary Pack: USP type-I Clear glass 10 mL.
Tubular vial stoppered by 13 mm double slotted rubber stopper and sealed by using 13 mm Flip-Off seals.

Method of Manufacture:
1. Dispense active and inactive ingredients as per formula.
2. Take required quantity of water for Injection (temperature of water at about 25±5° C.) in the mixing vessel and purge with nitrogen gas throughout the process (DO<2 ppm).
3. Add weighed quantity of TRIS and Citric Acid (as per individual formulation composition) to the above water for injection and dissolve by stirring.
4. Weigh accurately the required quantity of the bortezomib and transfer into measured quantity of acetonitrile into the separate mixing vessel and stir till it dissolves completely.
5. Add step-4 into step no-3 and stir till it dissolves completely.
6. Make up the final volume with Water for Injection and stir for 30-45 minutes until solution is uniform & check pH of the bulk solution.
7. Hold the solution with nitrogen blanket. After approval, filter the solution through 0.2 micron sterile filter
8. Fill the sterile bulk solution into the depyrogenated glass vials and partially stopper with sterile bromobutyl stoppers.
9. Lyophilize the partially stoppered vials in a freeze dryer.
10. After completion of lyophilization cycle, partially release vacuum & stopper the vials, followed by release the vacuum completely under nitrogen gas supply.
11. Unload the vials from lyophilizer and seal the vials with flip-off seals.

USP, per vial. Data below in the chart shows the reconstitution time of test formulation and comparative formulation with mannitol.

| | Reconstitution time | |
|---|---|---|
| Testing period | Comparative Formulation (Bortezomib & Mannitol) | Test Formulation F1 (Bortezomib, TRIS & Citric acid) |
| Initial | 1.3 min | <30 sec |
| 1 Month | 1.4 min | <30 sec |
| 2 Month | 1.5 min | <30 sec |
| 3 Month | 1.3 min | <30 sec |

Example 2: Stability of Reconstituted Solution of Formulation F1

Vials of finished product of example 1 reconstituted with required volume of 0.9% sodium chloride. The reconstituted solution was then stored at room temperature (RT). Product was then analyzed for increase in related substances at different intervals during storage and following are the results as shown below

| | Reconstitution stability (with 3.5 ml) at Room Temperature | | | | | |
|---|---|---|---|---|---|---|
| S No | Name of Imp | Initial | 3 hrs | 6 hrs | 9 hrs | 16 hrs | 24 hrs |
| 1 | Impurity-1 | 0.01 | 0.01 | 0.01 | 0.01 | 0.01 | 0.01 |
| 2 | Impurity-2 | ND | 0.01 | 0.03 | 0.04 | 0.06 | 0.08 |
| 3 | Impurity-5 | 0.01 | 0.01 | ND | 0.01 | 0.01 | 0.01 |
| 4 | Diastereomer | 0.01 | 0.01 | 0.01 | 0.01 | 0.01 | 0.01. |
| 5 | Impurity-6 | 0.03 | 0.04 | 0.04 | 0.04 | 0.05 | 0.07 |
| 6 | Impurity-3 | 0.02 | 0.02 | 0.02 | 0.02 | ND | ND |
| 7 | Impurity-7 | 0.02 | 0.02 | 0.03 | 0.04 | 0.05 | 0.04 |
| 8 | Impurity-4 | ND | ND | ND | ND | ND | ND |
| 9 | BZM-9 | ND | ND | ND | ND | ND | ND |
| 10 | Max Unknown | 0.14 | 0.13 | 0.13 | 0.13 | 0.14 | 0.14 |
| 11 | Total Impurity | 0.25 | 0.28 | 0.29 | 0.30 | 0.33 | 0.36 |

(ND = Not Detected)

TABLE 1

| | | 25° C./60% RH | | | | 40° C./75% RH | | | |
|---|---|---|---|---|---|---|---|---|---|
| | | | | Parameter | | | | | |
| | Reconstitution time | Impurity-1 (%) | Impurity-2 (%) | Impurity-3 (%) | Total impurities (%) | Impurity-1 (%) | Impurity-2 (%) | Impurity-3 (%) | Total impurities (%) |
| Bulk solution | — | 0.01 | ND | ND | 0.22 | 0.01 | ND | ND | 0.22 |
| Initial FP | <30 sec | 0.01 | 0.01 | ND | 0.24 | 0.01 | 0.01 | ND | 0.24 |
| 1M | <40 sec | 0.02 | 0.01 | ND | 0.3 | 0.03 | 0.05 | ND | 0.33 |
| 2M | <1 min | 0.02 | 0.02 | ND | 0.23 | 0.03 | 0.04 | ND | 0.24 |
| 3M | <1 min | 0.02 | 0.03 | ND | 0.28 | 0.04 | 0.08 | ND | 0.34 |

(ND = Not Detected)

The product obtained in example 1 was reconstituted with 0.9% NaCl solution. The pH of the solution was 4.08. Table-1 provides the stability data of the product.
The lyophilized composition of the present invention has an advantage of lesser reconstitution time when reconstituted with 0.9% sodium chloride solution compared with a composition which is pharmaceutically equivalent to VELCADE available on the market and prepared by the known methods. The pharmaceutical equivalent product used for this comparison has as inactive ingredient 35 mg mannitol,

Example 3

The product of example 1 was subjected to LC-MS/MS for characterization in the following manner.

Bortezomib composition obtained by lyophilization as such was dissolved in acetonitrile and subjected to Direct Insertion Probe-Mass Spectral analysis (positive ion, electrospray) using acetonitrile and water (90:10) as mobile phase.

Specification:

Instrument: AB SCIEX 4000 QTRAP® LC/MS/MS System

Solvent: Acetonitrile

Column: Symmetry Shield RP-18 (250 mm×4.6 mm×5 μm)

Mobile phase: Acetonitrile and water in the ratio (90:10)

Mass spectral analysis exhibited molecular ions at m/z 407, 470, and 541 which corresponds to sodium adduct of bortezomib, tris ester of bortezomib and citric acid ester of bortezomib respectively (FIG. 1).

This observation was further confirmed by subjecting bortezomib formulation to LSMS/MS analysis using Symmetry Shield RP-18 (250 mm×4.6 mm×5 μm) and acetonitrile and water (90:10) as mobile phase. The above LSMS/MS analysis was performed on AB SCIEX 4000 QTRAP® LC/MS/MS System.

Based on above LC-MS/MS study on bortezomib formulation and bortezomib API, it is concluded that the composition of example 1 is a mixture of bortezomib, tris ester of bortezomib and citric acid ester of bortezomib.

We claim:

1. A lyophilized pharmaceutical composition comprising Bortezomib or pharmaceutically acceptable salt or solvate thereof, tromethamine and citric acid or a salt thereof; wherein the pH of the composition is from about 3.0 to 6.0 upon reconstitution.

2. The composition according to claim 1, wherein the pH is from about 3.5 to 5.5.

3. The composition according to claim 2, wherein the pH is from about 4.0 to 4.5.

4. The composition according to claim 1, wherein the molar ratio of Bortezomib, tromethamine and citric acid is 1:1 to 15:1 to 11.

5. The composition according to claim 4, wherein the molar ratio of Bortezomib, tromethamine and citric acid is 1:4 to 10:4 to 8.

6. The composition according to claim 5, wherein the molar ratio of Bortezomib, tromethamine and citric acid is 1:7 to 8:5 to 6.

7. The composition according to claim 1, wherein the composition is reconstituted with water for injection or 0.9% sodium chloride.

* * * * *